United States Patent [19]

Remes et al.

[11] 4,019,966
[45] Apr. 26, 1977

[54] METHOD OF AMPEROMETRIC DETERMINATION OF THE CONCENTRATION OF ARENDIAZONIUM SALTS

[75] Inventors: Miroslav Remes; Miroslav Matrka; Zdenek Sagner, all of Pardubice, Czechoslovakia

[73] Assignee: Vyzkumny ustav organickych syntex, Pardubice, Czechoslovakia

[22] Filed: June 4, 1976

[21] Appl. No.: 583,632

[30] Foreign Application Priority Data

June 4, 1974 Czechoslovakia .............. 3947/74
Dec. 6, 1974 Czechoslovakia .............. 8345/74

[52] U.S. Cl. ........................... 204/1 T; 204/195 R
[51] Int. Cl.$^2$ ........................... G01N 27/46
[58] Field of Search ........... 204/1 T, 1 N, 1 K, 1 M, 204/195 R, 195 H, 195 T

[56] References Cited

UNITED STATES PATENTS

| 3,073,772 | 1/1963 | Wirz et al. ............... 204/195 R |
| 3,402,116 | 9/1968 | Kaltenhauser et al. .......... 204/195 |
| 3,574,079 | 4/1971 | Kalman .................. 204/195 R |
| 3,592,694 | 7/1971 | Urbach et al. ............... 204/1 N |

OTHER PUBLICATIONS

Kolthoff et al., "Polarography", vol. 2, pp. 776–778, 1952.

*Primary Examiner*—T. Tung

[57] ABSTRACT

Method of and apparatus for the amperometric determination of the concentration of arendiazonium salts in a diazocoupling reaction mixture. The apparatus has an external body in the bottom part of which cleaning material is disposed, a shaft, an inner body mounted on the shaft, at least two electrodes located in the inner body, a commutator, each of the electrodes being independently connected with one segment of the commutator. The commutator forms a component part of the shaft of the inner body; an electric motor is connected with the shaft to drive the inner body, compression bearings with a spring and an adjusting screw being disposed for adjustment of the compressive force between the inner body with its electrodes and the cleaning material. Brushes cooperate with the commutator for alternately connecting spaced pairs of electrodes on the inner body of the measuring circuit and disconnecting them therefrom.

2 Claims, 2 Drawing Figures

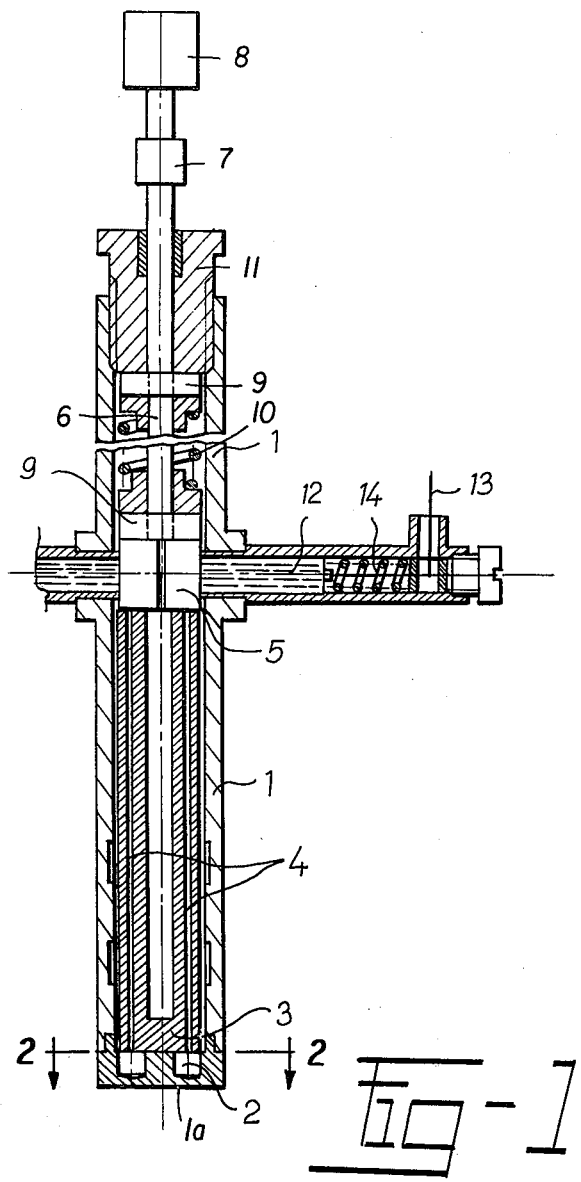
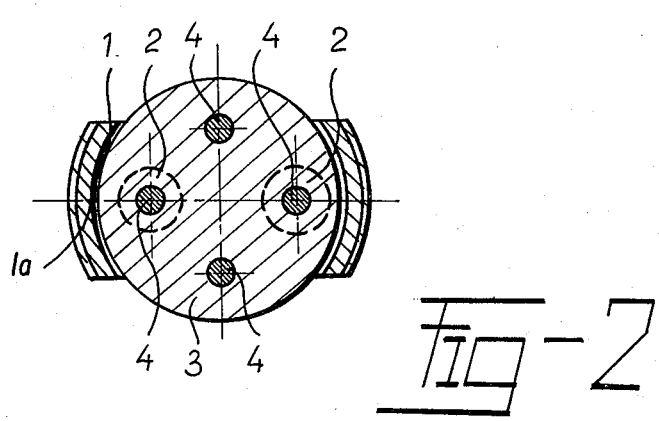

METHOD OF AMPEROMETRIC DETERMINATION OF THE CONCENTRATION OF ARENDIAZONIUM SALTS

This invention relates to a method of and an apparatus for amperometric determination of the concentration of arendiazonium salts by using a metal measuring electrode and a reference electrode with a loaded voltage.

More particularly, the apparatus according to the invention relates to an apparatus for amperometric determination of the concentration of arendiazonium salts in which the measuring electrode surface is periodically cleaned.

In higherto used methods in diazocoupling reactions, usually a solution of arendiazonium salt is charged step-by-step into the solution of a coupling component. The rate of charging of diazonium salt usually decreases at the end of the reaction owing to the speed of the reaction. The presence of an unreacted aromatic diazonium compound in the reaction mixture can be determined either by a visual method involving an external color dropping reaction on a filtration paper, usually using a solution of 2-naphthole-3,6-disulphonic acid, or by a method based on a polarographic reduction of arendiazonium salt on a mercury dropping electrode held at a suitable loaded voltage.

The disadvantage of the visual method for diazocoupling reaction, which is a final chemical reaction yielding azodyestuffs as a product, consists in the fact that an excess of arendiazonium salt causes a decomposition, the results of which are compounds of phenalic character and nitrogen. The products of decomposition cause not only a decrease in yield, but also a lowering in quality of the final dyestuff. In an opposite case, when a new corresponding charge of arendiazonium salt solution is introduced into the reaction mixture after the reaction between areadiazonium salt and coupling component has already finished, the reaction time is longer and therefore the production capacity of the apparatus used is lower.

In general, the visual test is sometimes not of high accuracy, takes a long time, and requires much experience from the point of apparatus attendance.

The disadvantage of amperometric determination of the concentration of arendiazonium salts with the polarographic reduction of arendiazonium salts using the mercury dropping electrode with a suitable loaded voltage consists above all in the necessity of using expensive and toxic mercury, and in most cases the treatment must be provided in an inert atmosphere of nitrogen to remove the maximum amount of disturbing oxygen.

It is very advantageous, from the point of electrode cleaning, that the electrode surface be regenerated during measurement, and that an accumulation of undesired compounds does not appear.

The main problem inherent is the toxicity of mercury, especially in plants where it is very difficult to remove contamination of products, semi-products and waste products with traces of mercury or compounds thereof. It seems that it will be impossible in the future, because of hygienic reasons, to use mercury electrodes.

The above-described disadvantages were reduced by using a copper measuring electrode for the amperometric reduction of arendiazonium salt, substituted with a group assuring solubility. Measuring using a copper electrode with a loaded voltage was described in Czechoslovakian Patent Application No. PV 2576-74. A disadvantage of such process resides in the fact that the limited current is dependent on a hydroxonium ion concentration, and that a high concentration of the electrolyte is undesirable from the points of view of diazocoupling reactions control and of the production of azodyestuffs.

The method and apparatus of the amperometric determination of arendiazonium salts obviates or mitigates the above-outlined disadvantages of the prior art.

In accordance with the present invention, there is provided a method for amperometric determination of the concentration of arendiazonium salts in the reaction mixture by the measurement of a limiting current flowing in the circuit which consists of a tellurium measuring electrode and a reference electrode with a loaded voltage ranging from $-0.05$ to $-0.5$V, and the periodic renovation of the surface of the measuring electrode. As a reference electrode there is usually used a saturated calomel electrode of disc shape. The measuring electrode may be either a stationary one or a rotating one with a periodic renovation of the electrode surface.

When the measuring electrode is of the stationary type, the arendiazonium salt which is to be determined must contain one or more solubilization groups (assuring solubility).

When a measuring electrode of the rotating type is used, it is possible to determine all types of arendiazonium salts, with the exception of chinondiazides, without any regard to the solubility thereof. Concentration of arendiazonium salts is determined by a current which is measured or registered with a recording milliameter. The concentration of arendiazonium salts is determined by means of the electrochemical reduction of the electrode used; through this, in the first stage, there results an arendiazonium radical which reacts with the measuring electrode to produce tellurium organic compounds.

The tellurium electrode permits a determination of only arendiazonium salts because the other compounds and reaction components stay inactive; this is a great advantage of the method described.

Analyzers containing tellurium measuring electrode may be used in the first place for purposes of measurement of the reaction kinetics of diazocoupling reactions in a wide range of pH values, ion strengths, and temperatures. The analyzers are also usable for analytical purposes, for example, for the determination of phenolic compounds, N-substituted aromatic and aliphatic amines, and compounds containing an active methylene group, etc., by titration with a volumetric solution of arendiazonium salts. A further advantageous application of the invention is its utilization for the automatic control of diazocoupling reactions.

The tellurium measuring electrode with attendant cleaning, employed for arendiazonium salts determination may be used universally. In accordance with the present invention, the surface of the measuring electrode is cleaned with a cleaning material during the movement of the electrodes, when the electrodes are being charged, are being connected in the measuring circuit, or are being disconnected from the measuring circuit.

Apparatus for performing the method of amperometric determination of the concentration of arendiazonium salts concentration according to the present invention includes an external body, in the bottom part of which a cleaning material is situated, an inner body in which at least two electrodes are disposed, each of the electrodes being independently connected with one segment of a commutator. The commutator forms a component part of the shaft of the inner body; the shaft is connected with an electric motor which rotates the inner body, which is mounted on the shaft. Compression bearings, a spring, and an adjusting sleeve-like nut are provided for the adjustment of the compression force between the inner body with its electrodes and the cleaning material.

The commutator is connected to outer terminals by means of brushes and compression springs, so as periodically to connect the electrodes to their alternating measuring circuit and to disengage it therefrom.

A preferred embodiment of the present invention will now be described by way of example with reference to the accompanying drawings which illustrate the invention:

FIG. 1 is a view in vertical cross-section of an apparatus for the periodic cleaning of the active surfaces of measuring electrodes; and FIG. 2 is a view in horizontal section through the apparatus of FIG. 1, the section being taken along the line 2—2 in FIG. 1.

The apparatus for the periodic cleaning of the measuring electrodes shown in the drawings includes an external sleeve-like body part 1 having a lower end member 1a provided with the cleaning material 2, an inner body 3, the shape of which is advantageously cylindrical, made of electro-insulating material, in which a plurality, advantageously four, tellurium electrodes 4 are fixed. Each of the electrodes 4 is conducted with a respective segment of the commutator 5. The commutator 5 is a component part of an inner body 3 which is mounted on a shaft 6 connected by a coupling 7 with an electric motor 8 for rotating the inner body 3. The shaft 6 is provided with compression bearings 9, a coil compression spring 10 and a threaded adjusting sleeve 11, which adjusts the compressive force between the inner body 3 with the electrodes 4 and the cleaning material 2. Brushes 12 assure the alteration of the engagement and disengagement of the electrodes into and out of the measuring circuit. The brushes 12 are pressed by the compressive springs 14 against the commutator 6 with a constant force. The brushes 12 are connected by springs 14 to terminals 13 providing for the connection of the electrodes 4 in the measuring circuit.

The electrode system in accordance with this invention may be employed for example in potentiometric, bipotentiometric, amperometric (i.e. polarometric) and biamperometric methods of measurement.

The external body 1, in the part where the electrodes 4 are situated may be of open frame shape, as shown, in the bottom part in which the cleaning material 2 is situated. The inner body 3 is made of electrically insulating material, as, for example, epoxide resin, in which there are advantageously four electrodes made, for example, of copper wire the diameter of which is about 2 mm. As above noted, each of the electrodes is connected to a respective segment of the commutator 5.

The commutator 5 is connected with the shift 6 which is connected by the coupling 7 with the electric motor 8 assuring the rotating motion of the inner body 3 so that the commutator 5 rotates simultaneously with the electrodes 4. The shaft 6 is provided with the compressive bearing 9 on which the spring 10 presses. The value of the compressive force of spring 10 is adjusted by means of the adjusting sleeve nut 11 above the further bearing 9 so as to provide a suitable compression force between the inner body 3 with the electrodes 4 and the cleaning material 2. As a cleaning material there may be used a brush of synthetic or glass fibers, felt, leather, or a hard grinding material, for example, Carborundum, etc. Usually the speed of rotation of the inner body ranges between 1 to 10 revolutions per second.

There are always connected two opposite electrodes 4 in the measuring circuit, wherein the lower end surfaces of such electrodes 4 are in contact with a reaction mixture (not shown), and two other electrodes are out of the measuring circuit and are being simultaneously cleaned. In the next period the cleaned electrodes are displaced into the position where they are out of the contact with the cleaning material 2 and are simultaneously and automatically connected through the commutator 5 into the measuring circuit. At that time the second pair of the electrodes 4 are cleaned and are disconnected from the measuring circuit.

From FIG. 2 it can be seen that the electrodes 4, in their measuring position, have portions of their respective end surfaces which are not covered by the lower end member 1a. Such uncovered portions, therefore, would contact the reaction mixture.

When the apparatus is used for bipotentiometric measurements, the pair of the electrodes 4 being used is polarized with a constant current, and the concentration of the measured compound corresponds to the difference of the potential between electrodes.

In biamperometric measurements, the electrodes 4 have a constant voltage, and the value of the concentration of the compound corresponds to the circuit flowing through the measuring circuit.

In amperometric and potentiometric measurements, the arrangement of the apparatus is the same as above-described but with the difference that opposite electrodes are connected in series so that the measuring electrode has a doubled surface area; a calomel electrode constitutes the other electrode in the measuring circuit.

In making amperometric measurements, a source of a direct current is interconnected in the measuring circuit, the reference electrode and the electric current flowing through the circuit corresponding to the value of the determined compound concentration.

It is an especially interesting point in this invention that the electrode surface is activated in the very short time interval when the electrodes are disconnected from the measuring circuit. This has very advantageous influence on a sensitivity, accuracy and stability of the obtained value of the concentration of the analyzed compound, and also in long-time industrial measurements.

The advantages of the invention consist in its general-purpose character, its easy application, its little need for maintenance, and the possibility of its use in the automatic control not only of analytic measurements, but also of chemical production.

The invention will now be illustrated by means of the following examples:

EXAMPLE 1

This concerns the diazometric titration of 1-(4-sulphophenyl)-3-methyl-5-pyrazolone of 0.05 M with a volumetric solution of 4-sulphobenzenediazoniumchloride by the use of a stationary tellurium electrode of disc shape and a reference calomel electrode with the loaded voltage of −250 mV in a medium of Britton-Robinson buffers, the pH value of which was 8.5 at a temperature of 25° C. The accuracy of the method was ± 0.2% with a charging rate of 1 ml/min, and total consumption of the solution of 10 ml, and a displacement rate of the recording paper of 10 mm/min.

EXAMPLE 2

The same electrode system as given in Example 4 was used for the kinetic measurement of the diazocoupling reaction of 4-sulphobenzenediazoniumchloride and 1-(4-sulphophenyl)-3-carboxy-5-pyrazolone.

Into a vessell 5 ml of 0.04 M solution of Britton-Robinson buffer, the pH value of which was 5.0, 0.5 ml of 0.35 M solution of tartrazine O and 43.9 ml of water were introduced. After stabilization of the current, 0.5 ml of 0.02 M solution of 4-sulphobenzenediazoniumchloride were added into the reaction vessel. Then the travel of the recording paper of the recorder was started, and simultaneously 0.1 ml of a 1 M solution of 1-(4-sulphophenyl)-3-carboxy-5-pyrazolone was added. The rate constants were calculated from the kinetic curve values.

EXAMPLE 3

For diazocoupling reaction control, a rotating tellurium electrode with a periodic renovation of the electrode surface was used. Into the reaction vessel, which was provided with an agitating device, 1000 ml of a 1 M solution of 1-(4-sulphophenyl)-3-carboxy-5-pyrazolone with a pH value of 6.5 was added and the pH value of the solution was brought to a value of pH 10. The rotating tellurium electrode and calomel electrode were connected with a polarograph with a linear recorder. The voltage was −250 mV. The rotation rate of the tellurium electrode was 1 revolution per second. After stabilization of the current, the control element of the recorder was set on a value which corresponded to 0.1% excess of 4-sulphobenzenediazoniumchloride in the reaction medium at the end of the reaction.

Simultaneously, the charging device was also adjusted to feed a maximum of 0.5 M of 4-sulphobenzenediazoniumchloride.

Immediately after an increase of 4-sulphobenzenediazoniumchloride concentration above the value to which the control element of the recorder was adjusted, the charging device was automatically switched off, and after the reaction was finished and the concentration lowered under the present value, the system was again switched on. At the stochiometric end point of titration (a miximum excess of 4-sulphobenzenediazoniumchloride of 0.1%), the charging device was permanently switched off. The reaction period was 5 minutes.

The method and apparatus in accordance with the present invention permits the construction of automatic analyzers which can measure the concentration of arendiazonium salts under production conditions, thereby permitting the automation of coupling reactions in azodyestuffs production.

Although the invention has been illustrated and described with reference to a plurality of preferred embodiments, it is to be expressly understood that it is in no way limited to the disclosure of such a plurality of embodiments, but is capable of numerous modifications within the scope of the appended claims.

What is claimed is:
1. In an amperometric method of determining the concentration of arendiazonium salts in a diazocoupling reaction mixture, the method comprising the steps of applying a DC voltage across a tellurium measuring electrode in contact with the mixture and a reference electrode so that only ions of arendiazonium salts in the mixture are reduced on the surface of the measuring electrode, measuring the resultant current through the measuring and reference electrodes, and periodically cleaning the measuring electrode.

2. A method as defined in claim 1, in which the periodically cleaning step is accomplished by continually rotating the tellurium electrode during the current measuring step between a measuring position and a cleaning position.

* * * * *